United States Patent [19]

Snyder, II, deceased et al.

[11] Patent Number: 4,816,597

[45] Date of Patent: Mar. 28, 1989

[54] DENTAL RESTORATIVE MATERIALS BASED UPON BLOCKED ISOCYANATES

[75] Inventors: William H. Snyder, II, deceased, late of Staten Island, N.Y., by Latricia Snyder; David Kristol, Aberdeen, N.J.

[73] Assignee: New Jersey Institute of Technology, Newark, N.J.

[21] Appl. No.: 946,683

[22] Filed: Jan. 5, 1987

Related U.S. Application Data

[63] Continuation of Ser. No. 656,951, Oct. 2, 1983, abandoned.

[51] Int. Cl.$^4$ .......................................... C07C 125/073
[52] U.S. Cl. ......................................... 560/25; 560/21; 560/22; 558/416
[58] Field of Search ............................ 560/25, 21, 22; 558/416

[56] References Cited

U.S. PATENT DOCUMENTS

| | | | |
|---|---|---|---|
| 3,020,249 | 6/1962 | Curtis | 260/2.5 |
| 3,254,411 | 6/1967 | Shelley | 32/15 |
| 3,825,518 | 7/1974 | Foster et al. | 260/998.11 |
| 3,862,920 | 1/1975 | Foster et al. | 260/998.11 |
| 3,997,592 | 12/1976 | Aufdermarsh, Jr. | 260/471 |
| 4,078,015 | 3/1978 | Leitheiser et al. | 560/25 |
| 4,089,763 | 5/1978 | Dart et al. | 204/159 |
| 4,191,834 | 3/1980 | Tucker | 548/305 |
| 4,192,762 | 3/1980 | Osborn | 252/182 |
| 4,225,696 | 9/1980 | Colpitts et al. | 528/76 |
| 4,243,578 | 1/1981 | O'Sullivan et al. | 260/998.11 |
| 4,281,992 | 8/1981 | Colpitts et al. | 433/212 |
| 4,330,283 | 5/1982 | Michl et al. | 433/201 |

FOREIGN PATENT DOCUMENTS 2080305 3/1982 United Kingdom .

*Primary Examiner*—Michael L. Shippen
*Attorney, Agent, or Firm*—Klauber & Jackson

[57] ABSTRACT

Novel blocked diisocyanate monomers are provided. These monomers are useful for filling dental cavities, for cementing teeth and for general dental restorative procedures.

Methods for preparing the monomers as well as methods for using them are described.

8 Claims, No Drawings

DENTAL RESTORATIVE MATERIALS BASED UPON BLOCKED ISOCYANATES

This application is a continuation, of application Ser. No. 656,951, filed Oct. 2, 1983 now abandoned.

BACKGROUND OF THE INVENTION

When tooth decay is noted, a dentist may remove the decay by drilling, cleaning out the cavity so formed in the tooth and then shaping the cavity to accept a filling material. The filling procedure has the purpose of sealing the cavity from its environment and also rebuilding the tooth to its previous shape and form. Conventional filling materials are e.g. amalgams, acrylate polymers and silicate compositions. A primary problem in filling cavities however, is sealing or bonding the filling material to the freshly exposed tooth surface. This surface is most usually the dentin layer of the tooth. If a filling is improperly sealed or bonded to the tooth surface, leakage will occur with the result that oral bacteria will enter the cavity area and eventually cause a decay under the filling. This results in the necessity of removing the filling and the new decay with the production of an even larger cavity which must then be filled.

Mercury amalgam filling materials have a tendency to corrode at the interface with the tooth, and the corrosion products form a seal with the tooth thereby significantly impeding the inflow of saliva and oral bacterial. These mercury containing corrosion products are themselves toxic, however, so this method of sealing is less than satisfactory. In addition, the amalgam fillings are excessively visible and do not match natural tooth colors.

Organic polymer filling materials, e.g. methacrylates and polymethacrylates, can be produced so that they form strong cavity filling materials. Also, these materials can be tinted so that they match the natural tooth color and become virtually indistinguishable from the natural tooth. In addition, these polymeric materials do not corrode and do not produce toxic products when they are present in the mouth. Unfortunately, these organic polymer filling materials do not bond strongly to the dentin tooth layer, thereby permitting secondary decay processes which result in the necessary cavity enlargement and refilling procedures as described above.

It would therefore be beneficial to provide compositions and a means for strongly and tightly sealing the tooth surface of a cavity to the preferrable organic polymer filling materials known in the art.

The present invention provides certain substances which may be utilized to strongly and tightly seal organic polymeric filling materials to the dentin tooth layer. The substances of the invention comprise sites which readily combine with dentin to produce strong covalent bonds. These substances also beneficially comprise an additional site which may be utilized to copolymerize with the known organic polymer filling materials. Thus, the organic polymer cavity filling materials essentially become chemically bonded to the dentin through the intermediacy of the novel substances of the invention. Other compositions are known in the art for bonding organic polymer filling materials to the exposed cavity surface; however, the present compositions have demonstrated superior bonding strengths when compared to the known compositions. Further details of this improved property are given below.

SUMMARY OF THE INVENTION

The primary object of the invention is to provide certain novel blocked isocyanate monomers which may be utilized to prepare dental cavities for filling with organic polymer filling materials. The monomers of the invention also find use in dental restorations and as dental adhesives. The monomers of the invention have the structural formulas I, II and III

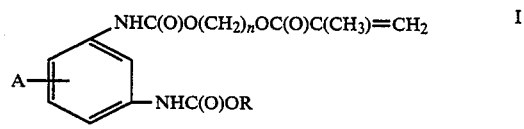

wherein
- A is alkyl having 1 to 6 carbon atoms;
- n is an integer of from 2 to 6; and
- R is 2-methoxy-4-allylphenyl or phenyl which may be substituted with one or two groups G
wherein
- G is methyl, halo, methoxy, nitro, carboxy, allyl or cyano;

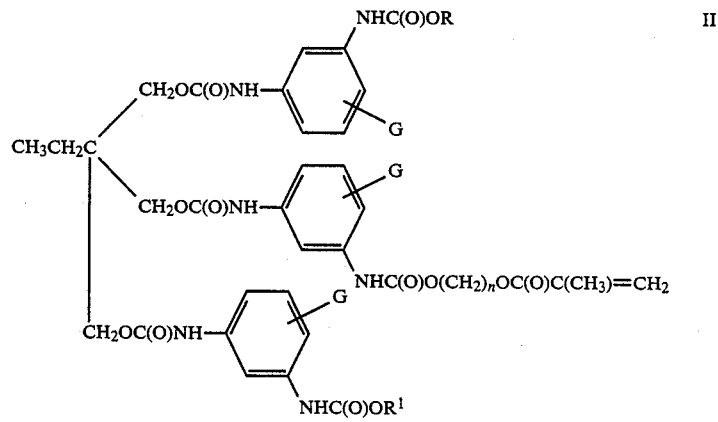

wherein
- R, G and n are as defined above; and
- $R^1$ is $O(CH_2)_nOC(O)C(CH_3)=CH_2$ or R;

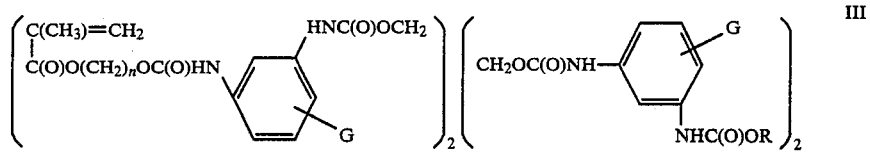

wherein
R, G and n are as defined above.

A second aspect of the invention contemplates the use of the monomers having structural formulas I, II and III to prepare dental cavities for filling with organic polymer filling materials.

A third aspect of the invention contemplates the use of the monomers having structural formulas I, II and III as dental adhesives.

Other aspects of the invention and uses for the monomers having structural formulas I, II and III will become clear upon reading the disclosure herein.

DETAILED DESCRIPTION OF THE INVENTION

The monomers of the invention having structural formula I may be prepared from readily available starting materials by methods well known to those skilled in the art.

For example, a phenyl diisocyanate such as 2,4-tolylene diisocyanate may first be reacted with an equivalent amount of an ω-hydroxyalkyl methacrylate ester such as 2-hydroxyethyl methacrylate or 6-hydroxyhexyl methacrylate. The product of this reaction will be a compound in which one of the isocyanate groups of the phenyl diisocyanate has reacted with the free hydroxyl group of the methacrylate ester thereby producing a mono-carbamate ester which is known to those skilled in the art as a urethane. This reaction is preferrably carried out in a solution utilizing a non-reactive solvent such as an alkane (e.g. pentane, hexane) or a mixture of alkanes may be used. Petroleum ether is a convenient solvent for this reaction. The use of a catalyst or a mixture of catalysts will aid this reaction. A mixture of chloranil and dibutyltin dilaurate is particularly useful for this purpose. The monocarbamate ester product may be isolated and purified, if desired, by standard techniques. For example, the product may be isolated by filtration and washed with fresh solvent to remove unreacted starting material.

The remaining isocyanate group of the monocarbamate ester is then blocked by reaction with a phenol such as o-, m- or p-cresol. This blocking reaction is preferably performed by just partially dissolving the monocarbamate ester in a non-reactive solvent (a mixture of ethyl acetate and petroleum ether, 3:5, is suitable) and then adding a solution of the desired phenol in a non-reactive solvent such as ethyl acetate. This reaction mixture is preferrably heated in an inert atmosphere to reflux temperature for sufficient time to complete the reaction. The product of this reaction, having structural formula I, may be isolated and purified, if desired, by standard methods.

The monomers having structural formula II may also be prepared from readily available starting materials using standard methods. Thus, trimethylolpropane is reacted with a phenyl diisocyanate using conditions which favor the production of a 3:1 adduct of diisocyanate to trimethylolpropane and minimize oligomer formation. Exemplary of such a method is to mix an excess of the diisocyanate in a non-reactive solvent (e.g. petroleum ether) to which a catalytic amount of dibutyltin dilaurate has been added. This mixture is rapidly stirred while a solution of trimethylolpropane in a non-reactive solvent (e.g. tetrahydrofuran) is slowly added. Additional petroleum ether is then added and stirring is continued. The addition of trimethylolpropane in tetrahydrofuran solution followed by the addition of a further amount of petroleum ether is repeated several times. The total reaction is preferrably carried out in an inert atmosphere using anhydrous conditions and purified solvents and starting materials. The product may be isolated and purified, if desired, by standard procedures. The product of this reaction, the 3:1 adduct of the diisocyanate to trimethylolpropane, has 3 unreacted isocyanate groups. These isocyanate groups are then converted to carbamate esters by reaction with a mixture of a phenol and an ω-hydroxyalkyl methacrylate using standard procedures. The ratio of phenol to methacrylate ester may be varied to produce a variety of monomers having structural formula II. The variation of this ratio will produce monomers having a range of desirable properties. The preferred ratio for purposes of the invention is 1:1.

The monomers having structural formula III may also be prepared from readily available starting materials. Thus, pentaerythritol is reacted with at least 4 moles of a phenyl diisocyanate to produce the corresponding 4:1 adduct wherein each of the 4 hydroxyl groups of pentaerythritol has reacted with an isocyanate group to produce a carbamate or urethane function. The reaction is preferrably carried out with rapid stirring and in dilute solution to favor reaction of only one isocyanate group per molecule of the phenyl diisocyanate reactant. The product is collected by standard means and may be washed with a solvent such as petroleum ether to remove unreacted starting materials. This 4:1 adduct is then dissolved in a convenient solvent such as tetrahydrofuran and treated with an approximate equimolar mixture of a phenol and an ω-hydroxyalkyl methacrylate such as 2-hydroxyethyl methacrylate using standard procedures to produce a monomer having structural formula III.

In use as sealing and bonding agents for organic polymer dental filling materials, the monomers of the invention are applied to the surface of the tooth cavity which has been prepared in the usual way. For example, after drilling the tooth cavity surface may be cauterized, sterilized and then dried. The monomers of the invention are then applied essentially by painting them on to the prepared cavity surface. The monomers of the invention which are liquid at room temperature may be applied directly in pure form. The monomers of the invention which are normally solid at room temperature are first dissolved in a suitable solvent such as dimethoxyethane or acetone, for example, and then applied. The solvent is then allowed to evaporate. The normally liquid monomers may also be applied as a solution if desired. Once applied, the monomers are permitted to react with the tooth surface for a period of from about 2 to about 10 minutes, preferably from about 2 to about 5 minutes. A standard organic polymer filling composition is then utilized to fill the cavity.

After polymerization is complete, the filling material may be shaped and polished in the usual manner. The filling so produced will be strongly and tightly bonded to the tooth surface, virtually eliminating the ingress of saliva and oral bacteria. Standard organic polymer filling compositions are known in the art, for example, a composition of 30% methyl methacrylate and 70% polymethyl methacrylate is particularly useful. Standard initiators such as benzoyl peroxide and standard promoters such as N,N-dimethyl-p-toluidine are utilized to aid the polymerization process. It is known that these polymers may be colored by the addition of certain agents such as titanium dioxide to match the color of the tooth. They may also be shaped and polished after curing by standard means.

The following test method was utilized to deomonstrate the strength of the bond formed between dentin and a standard organic polymer filling material using the monomers of the invention.

PREPARATION OF TEST SAMPLES

1. Aluminum Rods (Coupons)

The coupons are sanded with 320 grid sandpaper in order to remove undesired surface contaminants. The surface of the coupon is roughened by sandblasting, washed with acetone for five minutes, degreased with petroleum ether in an ultrasound cleaner, etched with a solution composed of sodium dichromate and concentrated sulfuric acid at room temperature for eight minutes, washed with water and dried on a hot plate.

2. Dentin Slices

Slices of dentin, 400 microns thick, are etched with, for example, a solution of 6.8% aqueous ferric oxalate for 30 seconds to 2 minutes, washed with water, and washed with 1,2-dimethoxyethane.

3. Bonding of the Blocked Isocyanate

The etched slice of dentin is submerged in a solution containing 1.5 grams of the blocked isocyanate monomer of the invention in 5 ml of 1,2-dimethoxyethane. After 15 minutes the dentin slice is rinsed with fresh 1,2-dimethoxyethane.

4. Polymerization

To 2 grams of a solution containing 30% methyl methacrylate 70% polymethyl methacrylate by weight are added 8 drops of N,N-dimethyl-p-toluidine. The solution is mixed and 20 mg of benzoyl peroxide are added. The solution is mixed again and spread onto the dentin slices and coupons.

The dentin slices are then sandwiched between two coupons and placed into a jig designed to accommodate six coupon-dentin sandwiches. A load of 1875 g is placed on the jig. The coupon-dentin sandwiches are allowed to sit for 12 hours, then placed in distilled water for one week at room temperature.

The coupons were then attached to universal joints, and pulled to fracture by a Scott tester operated at a cross head speed of 1 mm/minute.

Utilizing this procedure, the monomers of the invention were found to have improved bonding characteristics when compared to bonding materials known in the art.

The monomers of the invention are stable under normal conditions and may be stored in pure form for long periods of time without affecting their usefulness. Alternately, the monomers may be mixed with other excipients such as diluents, extenders, coloring agents and the like to produce compositions useful for preparing dental cavity filling materials, dental adhesives and materials useful for general dental restorative purposes.

EXAMPLES

EXAMPLE I

A monomer corresponding to structural formula I was prepared by the following procedure.

In a reaction flask equipped with a stirrer, water condenser and nitrogen inlet 69.6 grams (0.400 mole) of 2,4-tolylene diisocyanate (TDI), 0.15 grams chloranil and 0.07 grams dibutyltin dilaurate (DBTDL) were dissolved in 450 milliliters of petroleum ether. 52.1 grams (0.400 mole) 2-hydroxyethyl methacrylate (HEMA) were dissolved in 450 milliliters petroleum ether and placed in an addition funnel and slowly added to the reaction mixture with stirring.

During the course of the HEMA addition, a precipitate of mono HEMA-TDI adduct began to form in the slightly exothermic reaction mixture. Upon completion of the HEMA addition, the mixture was stirred at high speed for three hours, after which the precipitate was allowed to settle. The petroleum ether was removed and the precipitate washed twice with additional petroleum ether to remove unreacted TDI and HEMA.

Ethyl acetate, 150 milliliters, and 250 milliliters of petroleum ether were added to the precipitate in order to partially dissolve it. A solution of 43.7 grams (0.404 mole) of p-cresol in 50 milliliters of ethyl acetate was added to the mixture over a period of 30 minutes. The mixture was stirred for eight hours at 45° C. in a nitrogen atmosphere, then cooled to room temperature.

The solid which was obtained by removal of the solvent was washed with toluene and dried.

In a similar fashion, monomers containing 2-hydroxyethyl methacrylate, 3-hydroxypropyl methacrylate and 6-hydroxyhexyl methacrylate as the olefin to be polymerized and o-cresol, p-cresol, o-chlorophenol, m-chlorophenol, p-chlorophenol and eugenol as the phenolic blocking agent have been prepared.

EXAMPLE II

In this Example, a monomer having structural formula II was prepared. Accordingly, 234 grams (1.34 mole) of 2,4-tolylene diisocyanate (TDI) were mixed with 550 milliliters of petroleum ether and 14 drops of dibutyltin dilaurate (DBTDL). The solution was stirred for 30 minutes in a nitrogen atmosphere. 18.3 grams (0.136 mole) of trimethylolpropane (TMP) which had been dried in vacuo for 12 hours, was dissolved in 135 milliliters of tetrahydrofuran (THF), which had been purified by distilling from lithium aluminum hydride, and placed in an addition funnel. The TMP-THF solution was added dropwise at a rate of 18 milliliters per hour to the TDI-petroleum ether solution which was stirred at 15,000 RPM and maintained at 20° C. After one hour an additional 450 milliliters of petroleum ether was added. The addition of TMP-THF followed by petroleum ether was repeated several times in order to ensure the formation of a fine precipitate which is free of oligomers. A total volume of 1100 milliliters had been added by the end of the reaction.

The precipitate, which was allowed to settle out, was separated from the supernatant, treated three times with 500 milliliters of petroleum ether and dried at 25° C. for 18 hours.

25.0 grams (0.0381 mole) of TMP-TDI adduct were dissolved in 100 milliliters of tetrahydrofuran (THF). To this solution were added 13.8 grams (0.0840 mole) of eugenol, 7.84 grams (0.0602 mole) of 2-hydroxyethyl methacrylate (HEMA) and seven drops of dibutyltin dilaurate. The solution was flushed with nitrogen, the flask was sealed, and the system was kept at 50° C. for 12 days.

200 milliliters of THF were added. The precipitate was filtered, washed several times with petroleum ether and dried in vacuum at room temperature yielding a product which contains on the average 1.5 moles of HEMA and 1.5 moles of eugenol per mole of TMP-TDI.

In a similar fashion, combinations of TMP-TDI with HEMA and o-chlorophenol, p-chlorophenol, o-cresol and p-cresol have been prepared.

EXAMPLE III

Monomer having structural formula III 0.50 moles of pentaerythritol and 2.5 moles of 2,4-tolylendiisocyanate were dissolved in 400 ml of dioxane. Ten drops of dibutyltin dilaurate (DBTDL) added. The solution was kept at room temperature under nitrogen while stirred at high speed for 24 hours, at which time it was added to 1000 ml of petroleum ether. The precipitate of pentaerythritol-tolylenediisocyanate (PE-TDI) was collected and washed with more petroleum ether.

The dried precipitate was dissolved in tetrahydrofuran in a ratio of 50 ml of tetrahydrofuran (THF) per 9.60 mmole of PE-TDI. To this solution were added 19.8 mmole of 2-hydroxyethyl methacrylate and 24 mmole of substituted phenol, together with 5 drops of DBTDL.

The reaction mixture was maintained at 50° C. for 9 days under $N_2$.

100 ml of THF and 700 ml of petroleum ether were added to cause precipitation of the product. The precipitate was collected, washed with petroleum ether and dried.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

We claim:

1. A monomer having the structural formula I

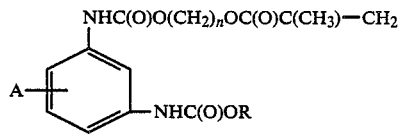

wherein
A is alkyl having 1 to 6 carbon atoms;
R is o,p methoxyphenyl and n is 2.

2. A monomer having the structural formula II

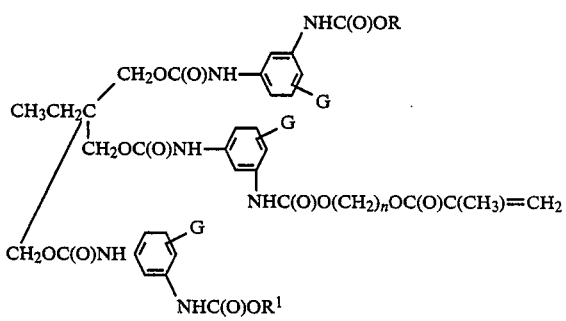

wherein n is an integer of from 1 to 6 carbon atoms; R is 2-methoxy-4-allylphenyl or phenyl which may be substituted with one or two groups G, wherein G is methyl, halo, methoxy, nitro, carboxy, allyl or cyano.

3. The monomer defined in claim 2 wherein G is methyl; R is o,p-tolyl, o,p-chlorophenyl, or —O(CH$_2$)$_2$OC(O)C(CH$_3$)=CH$_2$, provided that at least one R group is o,p-tolyl or o,p-chlorophenyl.

4. The monomers defined in claim 3 wherein R is o,p-chlorophenyl or o,p-tolyl.

5. The monomers defined in claim 3 wherein n is 2 and one R group is —O(CH$_2$)$_2$OC(O)C(CH$_3$)=CH$_2$.

6. The monomers defined in claim 3 wherein one R group is —O(CH$_2$)$_2$OC(O)C(CH$_3$)=CH$_2$, and the remaining R group is 2-methoxy-4-allylphenyl.

7. The monomers having the following structural formula III

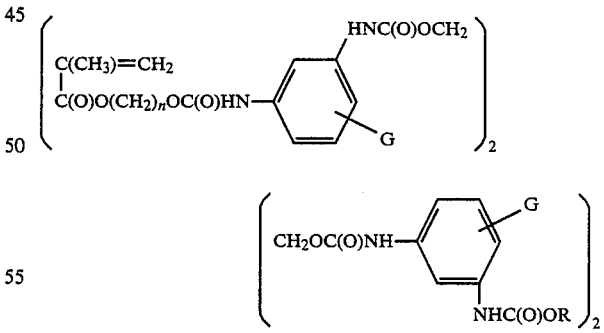

wherein n is an integer of from 2 to 6; and R is 2-methoxy-4-allylphenyl or phenyl which may be substituted with one or two groups G, wherein G is methyl, halo, methoxy, nitro, carboxy allyl or cyano.

8. The monomers defined in claim 7 wherein G is methyl.

* * * * *